(12) United States Patent
Horkheimer

(10) Patent No.: US 9,797,861 B2
(45) Date of Patent: Oct. 24, 2017

(54) MAGNETIC STIMULUS OF ISFET-BASED SENSOR TO ENABLE TRIMMING AND SELF-COMPENSATION OF SENSOR MEASUREMENT ERRORS

(71) Applicant: Honeywell International Inc., Morris Plains, NJ (US)

(72) Inventor: Donald Horkheimer, Minneapolis, MN (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/233,392

(22) Filed: Aug. 10, 2016

(65) Prior Publication Data

US 2016/0349209 A1    Dec. 1, 2016

(51) Int. Cl.
*G01N 27/414* (2006.01)
*G01N 27/416* (2006.01)

(52) U.S. Cl.
CPC ....... *G01N 27/4148* (2013.01); *G01N 27/414* (2013.01); *G01N 27/4165* (2013.01); *G01N 27/4167* (2013.01); *G01N 27/4168* (2013.01)

(58) Field of Classification Search
CPC ............ G01N 27/414; G01N 27/4163; G01N 27/4167; G01N 27/30
See application file for complete search history.

(56) References Cited

U.S. PATENT DOCUMENTS

| 4,851,104 A | 7/1989 | Connery et al. |
|---|---|---|
| 4,879,517 A | 11/1989 | Connery et al. |
| 5,068,205 A | 11/1991 | Baxter et al. |
| 5,407,854 A | 4/1995 | Baxter et al. |
| 5,414,284 A | 5/1995 | Baxter et al. |
| 6,117,292 A | 9/2000 | Ahmad |
| 6,623,616 B1 * | 9/2003 | Malver ............ G01N 17/00 204/404 |
| 8,329,104 B2 | 12/2012 | Lehmann et al. |

(Continued)

FOREIGN PATENT DOCUMENTS

| EP | 2518483 | 10/2012 |
|---|---|---|
| JP | 10227759 | 8/1998 |

(Continued)

OTHER PUBLICATIONS

European Patent Office, "Extended European Search Report from EP Application No. 15158717.7 dated Aug. 3, 2015", from Foreign Counterpart of U.S. Appl. No. 14/227,368, dated Aug. 3, 2015, pp. 113, Published in: EP.

(Continued)

*Primary Examiner* — Stephen Bradley
(74) *Attorney, Agent, or Firm* — Fogg & Powers LLC

(57) ABSTRACT

An ion sensor apparatus comprises at least one ion sensitive field effect transistor (ISFET) device configured to be exposed to a liquid, a reference electrode configured to contact the liquid to which the ISFET device is exposed, and at least one magnet configured to intermittently expose the ISFET device to a magnetic field. A processor is operatively connected to the ISFET device and the reference electrode. The processor modulates the magnetic field to produce a corresponding modulated output in resistance of the ISFET device, and modulation of a reported output value of the ion sensor apparatus.

12 Claims, 6 Drawing Sheets

(56) References Cited

U.S. PATENT DOCUMENTS

| | | | |
|---|---|---|---|
| 8,815,078 B2 | 8/2014 | Yamada et al. | |
| 2010/0231211 A1* | 9/2010 | Edelstein | G01D 1/00 324/244 |
| 2010/0301398 A1* | 12/2010 | Rothberg | G01N 27/4145 257/253 |
| 2011/0091870 A1* | 4/2011 | Lang | G01N 33/54393 435/6.11 |
| 2011/0100810 A1* | 5/2011 | Merz | G01N 27/227 204/406 |
| 2011/0127583 A1* | 6/2011 | Uhlig | G01R 33/07 257/252 |
| 2012/0273845 A1 | 11/2012 | Brown et al. | |
| 2013/0034880 A1* | 2/2013 | Oldham | C12Q 1/6853 435/91.5 |
| 2013/0075724 A1* | 3/2013 | Hirler | H01L 27/22 257/48 |
| 2015/0007007 A1 | 1/2015 | Byron et al. | |
| 2015/0024508 A1 | 1/2015 | Horkheimer et al. | |
| 2015/0070007 A1* | 3/2015 | Kurniawan | G01R 35/00 324/251 |
| 2015/0101938 A1 | 4/2015 | Bychkova et al. | |
| 2015/0276662 A1 | 10/2015 | Horkheimer | |

FOREIGN PATENT DOCUMENTS

| | | |
|---|---|---|
| KR | 20120042236 | 5/2012 |
| KR | 1020120042236 | 5/2012 |
| KR | 101179143 | 8/2012 |

OTHER PUBLICATIONS

European Patent Office, "Communication under Rule 71(3) EPC from EP Application No. 15158717.7 dated Jun. 27, 2016", from Foreign Counterpart of U.S. Appl. No. 14/227,368, dated Jun. 27, 2016, pp. 132, Published in: EP.

U.S., "Notice of Allowance", U.S. Appl. No. 14/227,368, dated May 19, 2016, pp. 1-13, Published in: US.

U.S., "Office Action", U.S. Appl. No. 14/227,368, dated Oct. 1, 2015, Published in: US.

"Outline of semiconductor magnetoresistive element", retrieved from Internet on Jan. 16, 2014 <http://www.akm/com/akm/en/product/add/magnetic_sensors/0086/>, pp. 1-2, pp. 1-2.

Bergveld, "Thirty years of Isfetology What happened in the past 30 years and what may happen in the next 30 years", Sensors and Actuators B 88, 2003, pp. 120, Publisher: Elsevier Science B.V.

Cao et al., "Silicon Nanowire-Based Devices for Gas-Phase Sensing", Sensors, Dec. 24, 2013, pp. 245-271, vol. 14.

Chaudhry et al., "Ultra-Low Contact Resistance of Epitaxially Interfaced Bridged Silicon Nanowires", Nano Letters, May 27, 2007, pp. 1536-1541, vol. 7, No. 6, Publisher: American Chemical Society.

Chiesi et al., "Chopping of a weak magnetic field by a saturable magnetic shield", Sensors and Actuators A 60, 1997, pp. 59, Publisher: Elsevier Science S.A.

Comini, "Metal oxide nano-crystals for gas sensing", Analytica Chimica Acta, Jun. 2006, pp. 28-40, Publisher: Elsevier.

Du et al, "InAs Nanowire Transistors as Gas Sensor and the Response Mechanism", Nano Letters, Oct. 2009, pp. 4348-4351, Publisher: American Chemical Society.

"7777 Style Durafet III Electrode Mounting with Vario Pin Connector Specification", Aug. 2004, pp. 14, Publisher: Honeywell Inc.

Janata, "Potentiometric Microsensors", Chemical Reviews, 1990, pp. 691-703, vol. 90, No. 5, Publisher: American Chemical Society.

Kyo et al., "Trial of Hydrothermal Plume Sensing Using Newly Developed ISFET pH Sensor", Celebrating the Past, Teaming Toward the Future, Sep. 22, 2003, pp. 1732-1737, Publisher: MTS/IEEE, Published in: JP.

Lebris et al, "Automated pH-ISFET Measurements Under Hydrostatic Pressure for Marine Monitoring Application", Feb. 6, 1997, pp. 205-215, vol. 356, No. 2-3, Publisher: Analytica Chimica Acta, Published in: FR.

Schwamb et al., "On the effect of the electrical contact resistance in nanodevices", Applied Physics Letters, Jun. 17. 2008, pp. 243106-1 to 243106-3, vol. 92.

Simon et al., "Autocalibration of silicon Hall devices", Sensors and Actuators A 52, 1996, pp. 203-207, Publisher: Elsevier Science S.A.

Tarasov et al., "Sensing With Silicon Nanowire Field-Effect Transistors", Jan. 1, 2009, p. 1, Publisher: NanowireSensor, Published in: CH.

Horkheimer et al, "Appartus and Method for Compensating pH Measurement Errors Due to Pressure and Physical Stresses", U.S. Appl. No. 13/947,924, filed Jul. 22, 2013, Jul. 22, 2013, pp. 1-39.

* cited by examiner

MAGNETIC STIMULUS OF ISFET-BASED SENSOR TO ENABLE TRIMMING AND SELF-COMPENSATION OF SENSOR MEASUREMENT ERRORS

CROSS REFERENCE TO RELATED APPLICATION

This application is a divisional of U.S. application Ser. No. 14/227,368 entitled MAGNETIC STIMULUS OF ISFET-BASED SENSOR TO ENABLE TRIMMING AND SELF-COMPENSATION OF SENSOR MEASUREMENT ERRORS, filed on Mar. 27, 2014, which is incorporated herein by reference.

BACKGROUND

An Ion Sensitive Field Effect Transistor (ISFET) device is typically implemented in a pH sensor used for measuring ion concentrations in solution. When the ion concentration (such as $H^+$) in the solution changes, the current through the ISFET device will change accordingly. The solution is used as the gate electrode of the transistor formed by the ISFET device.

In the environment of deep sea pH sensing, large cyclic pressure changes over depth can lead to deformation and creep of pH sensor packaging that includes an ISFET sensor die. This mechanical change of the pH sensor packaging can alter the stresses on the sensor die and changes its resistance due to piezoresistance effects. These changes are not readily predictable and cannot be compensated for in the initial calibration of the pH sensor in the factory. In addition, changes in the pH sensor are typically not directly observable over time, which can lead to poor performance over the lifetime of the pH sensor.

SUMMARY

An ion sensor apparatus comprises at least one ion sensitive field effect transistor (ISFET) device configured to be exposed to a liquid, a reference electrode configured to contact the liquid to which the ISFET device is exposed, and at least one magnet configured to intermittently expose the ISFET device to a magnetic field. A processor is operatively connected to the ISFET device and the reference electrode. The processor modulates the magnetic field to produce a corresponding modulated output in resistance of the ISFET device, and modulation of a reported output value of the ion sensor apparatus.

BRIEF DESCRIPTION OF THE DRAWINGS

Features of the present invention will become apparent to those skilled in the art from the following description with reference to the drawings. Understanding that the drawings depict only typical embodiments and are not therefore to be considered limiting in scope, the invention will be described with additional specificity and detail through the use of the accompanying drawings, in which.

DETAILED DESCRIPTION

Figure 1:
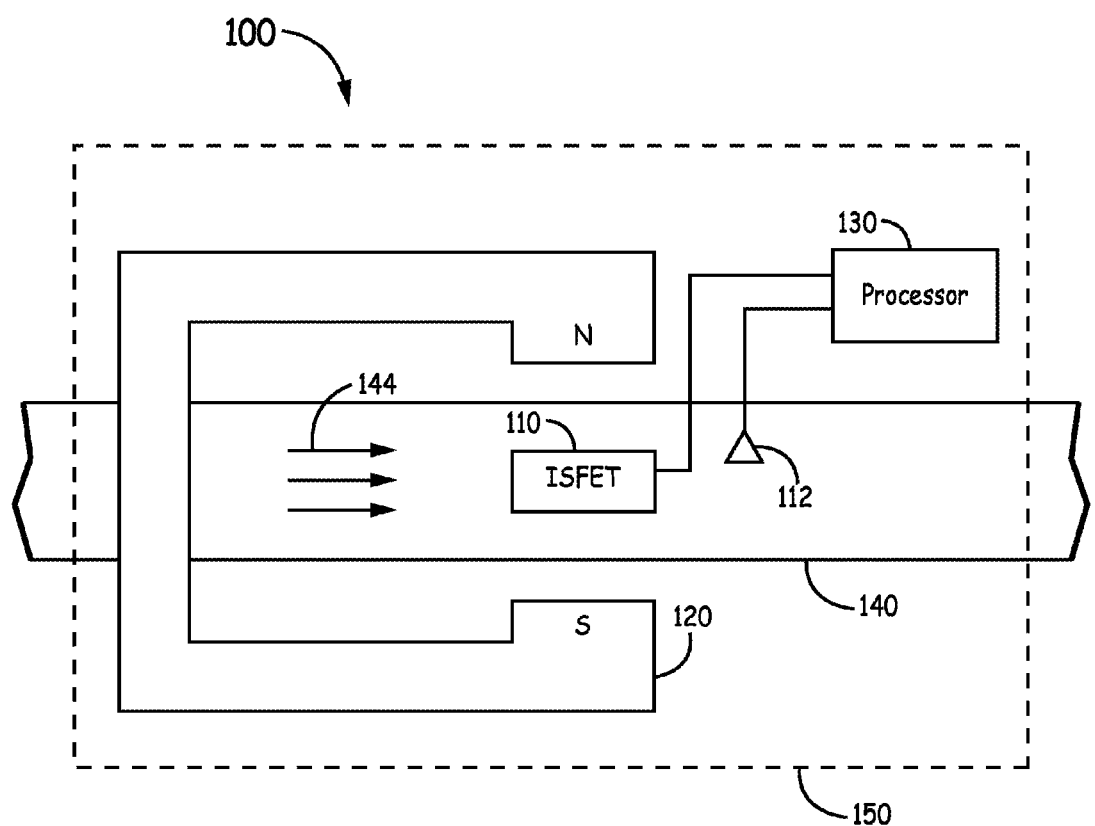
FIG. 1 is a schematic diagram of an ion sensor apparatus according to one embodiment.

In the following detailed description, embodiments are described in sufficient detail to enable those skilled in the art to practice the invention. It is to be understood that other embodiments may be utilized without departing from the scope of the invention. The following detailed description is, therefore, not to be taken in a limiting sense.

An ion sensor apparatus is provided that utilizes Ion Sensitive Field Effect Transistor (ISFET) technology along with a magnetic stimulus to enable trimming and self-compensation of sensor measurement errors. In one embodiment, the ion sensor apparatus can be implemented as a pH sensor for liquids.

The ion sensor apparatus generally includes at least one packaged ISFET die, a reference electrode, an optional counter electrode, and a voltage/current supply to provide power to the ISFET die. A processor connects the ISFET die and the electrodes in order to make a pH measurement. The ion sensor apparatus further includes a magnet for applying the magnetic stimulus to the ISFET die. Error compensation software is implemented by the processor to apply compensation for sensor errors based on the magnetic stimulus.

In one embodiment, the magnet is an electromagnet that has at least one coil of wire. A power supply can be provided to drive the coil of wire to create an electromagnetic field to which the ISFET die is exposed.

In another embodiment, one or more permanent magnets are employed to generate the magnetic field. To produce a "chopper" effect of being able to turn off and on the magnetic field, and measure the ISFET die response, the permanent magnet can be moved closer or further away from the ISFET die, or a magnetic shield can be periodically placed between the magnet and the ISFET die to alter the magnitude of the magnetic field. While permanent magnets are less controllable, they do not consume electrical energy, which is beneficial for applications with limited power available.

In addition, a sealed magnetic field sensor (e.g., not exposed to liquid or pressure) can be employed to provide feedback on the magnitude/state of the magnetic field. With application of the magnetic stimulus, essentially constant levels of pH can be measured, and corrupting influences like temperature, pressure, and mechanical changes on the ISFET die can be trimmed out.

To one skilled in the art of semiconductors it is known that the velocity by which electrons and holes move through a semiconductor is proportional to the carrier mobility of the semiconductor material. Different semiconductors have different inherent levels of mobility. It is also known that the electrical conductivity/resistivity of a semiconductor is proportional to the semiconductor's mobility. Changing mechanical stresses and temperature can impact the mobility of carriers leading to changes to resistance, which leads to changes in measured pH.

It is also known that magnetic fields can influence the flow of carriers through a material and in particular semiconductors. This effect is exploited to create Hall effect sensors. The Hall effect relies on the phenomenon that given a flow of carriers along one axis and a magnetic field applied about an axis perpendicular to the first axis, the carriers will start flowing towards a third perpendicular axis. This distortion of the carrier flow results in a Hall potential voltage that can be measured along this third axis. In the axis in which the carriers were originally and predominately flowing, the distortion of the carrier flow gives rise to an apparent increase in resistance along this axis.

The present technique is not concerned about the Hall potential that is generated in the off axis, but in the change in resistance that occurs as carriers flow through the ISFET device from source to drain through the gate connection, that is, their normal direction of flow. A change in voltage can be measured due to the change in resistance from source to drain in the ISFET device.

In the present approach, a modulated magnetic field is applied to produce a corresponding modulated output in resistance of the ISFET device and modulation of the reported pH value. The applied magnetic field can be used as a "chopper" signal to provide a known input excitation that should produce an expected output. When there is a difference between the actual output and the expected output, compensation can be applied to null this difference over time, thereby maintaining sensor stability.

One feature of the magnetic stimulus is that the signal it generates in the ISFET die is passed onto signal conditioning components (e.g., microprocessor, analog to digital converters, amplifiers, etc.). In addition, changes to the performance of these components with time due to aging are rolled into the error in pH sensing at the ISFET channel. Therefore, the present approach can also be used to trim these other drift terms that are normally not correctable.

In one implementation, the ion sensor apparatus can be employed as a pH sensor for deep sea/oceanographic instrumentation research. In this implementation, the pH sensor can be made robust enough to work at depths of about 6000 m for up to about 5 years, while maintaining exceptional stability and sensor accuracy.

Further details of the present ion sensor apparatus are described hereafter with reference to the drawings.

FIG. 1 illustrates a sensor apparatus 100 for sensing ions in a liquid according to one embodiment. The sensor apparatus 100 generally includes at least one ISFET device 110 configured to be exposed to the liquid, a reference electrode 112 configured to contact the liquid, at least one magnet 120, and a processor 130 operatively connected to ISFET device 110 and reference electrode 112. The magnet 120 is configured to intermittently expose ISFET device 110 to a magnetic field.

In one embodiment, ISFET device 110 is disposed within a flow tube 140 that is configured to receive flowing liquid designated by arrows 144. The reference electrode 112 is also in communication with the liquid inside flow tube 140.

The processor 130 modulates the magnetic field to produce a corresponding modulated output in resistance of ISFET device 110 and modulation of a reported output value of sensor apparatus 100.

In one exemplary implementation, ion sensor apparatus 100 is configured to be submersed in sea water, such as for deep sea pH sensing. As such, the various components of ion sensor apparatus 100 can be packaged in a water tight housing structure 150 that is able to withstand deep sea conditions. Other exemplary implementations for sensor apparatus 100 include ion sensing of ground water, industrial chemicals, refined chemicals, crude oil, or the like.

In a method of compensating for ion sensor measurement errors in sensor apparatus 100, ISFET device 110, while in contact with a liquid, is exposed to a magnetic field from magnet 120. This produces a corresponding output in resistance of ISFET device 110. This actual output of ISFET device 110 is monitored by processor 130 to determine whether there is a difference between the actual output and an expected output based on the magnetic field, and an error compensation value is determined when a difference in the outputs is detected. The error compensation value is then applied to null the difference between the actual output and the expected output over a period of time to maintain stability of the ion sensor measurements.

Figure 2:
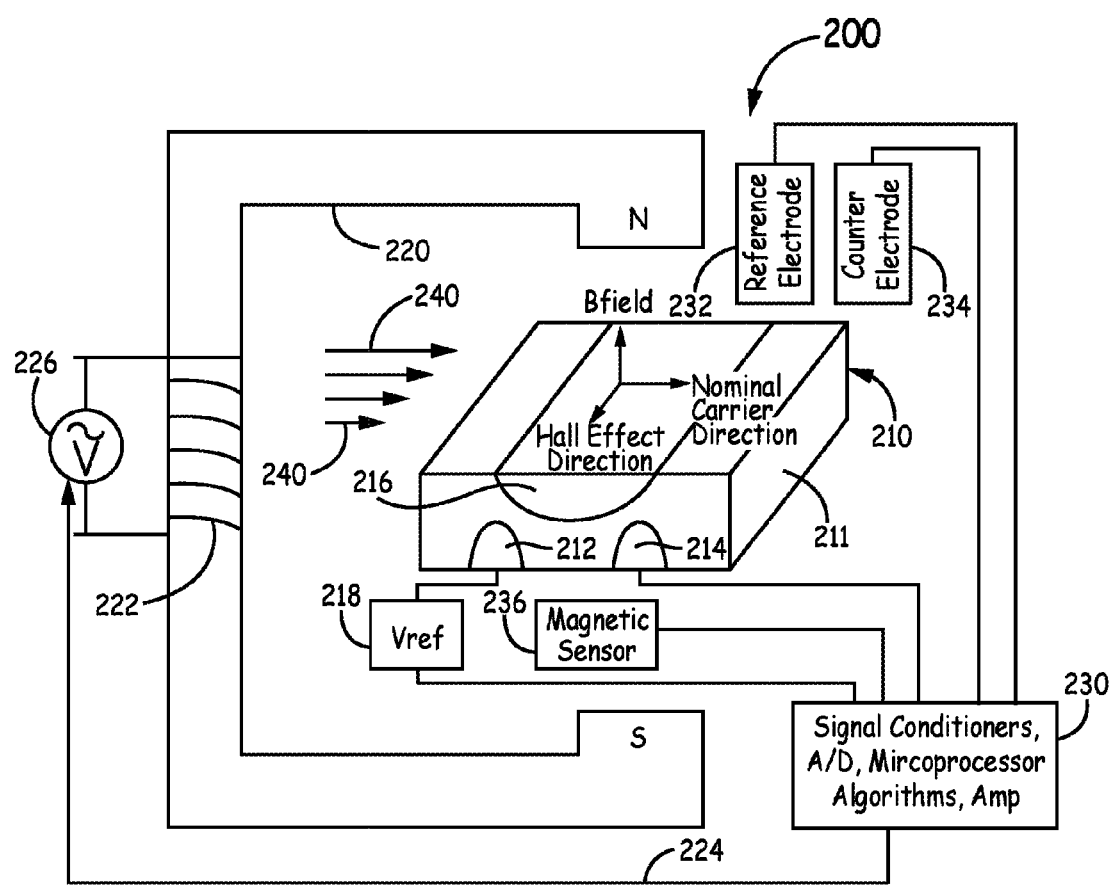
FIG. 2 is a schematic diagram of an ion sensor apparatus according to another embodiment.

FIG. 2 illustrates an ion sensor apparatus 200 according to another embodiment. The sensor apparatus 200 generally includes an ISFET die 210 configured to be exposed to a liquid, an electromagnet 220 configured to expose ISFET die 210 to a magnetic field, and a processor unit 230 operatively connected to ISFET die 210 and electromagnet 220.

The ISFET die 210 includes a semiconductor substrate 211 such as a silicon substrate. A source 212, a drain 214, and an ion sensitive gate channel 216 are formed in semiconductor substrate 211 with conventional techniques. The source 212 is electrically connected to a voltage reference source 218, which is coupled to processor unit 230. The drain 214 is electrically connected to processor unit 230. The ISFET die 210 is configured such that during operation of sensor apparatus 200, a nominal carrier direction is in a first direction, a magnetic field is in a second direction perpendicular to the first direction, and a Hall effect is in a third direction perpendicular to the first and second directions, as shown in FIG. 2.

In another embodiment, the drain and source connections on the ISFET die can be reversed with a switch, so that the nominal direction the carriers flow can be reversed. Combining this with different strategies for changing the sign of the magnetic field vector can be used to cancel out biases in the sensor output. Some errors, such as Ettinghausen, Peltier, and Joule heating errors, can be reduced by this method.

The electromagnet 220 includes at least one wire coil 222 that generates an electromagnetic field when power is applied. In one embodiment, a coil of wire can be placed around ISFET die 210 to produce the electromagnet field. A stable AC or DC power supply can be provided to drive wire coil 222, and a precision ammeter or voltmeter can be implemented to measure the current or voltage across wire coil 222. In one embodiment, a voltage control signal line 224 connects processor unit 230 to a voltmeter 226 coupled to wire coil 222. The electromagnet 220 is selectively activated by processor unit 230 to intermittently expose ISFET die 210 to the electromagnetic field produced by electromagnet 220.

In another embodiment, electromagnet 220 can include two or more coils. For example, two concentric and parallel offset coils can be used to create a uniform and intense magnetic field. Pairs of these coils aligned to orthogonal axes can create a multi-axis Helmholtz coil that allows magnetic fields to be generated with an arbitrary magnetic vector orientation in space. This allows for controlling the direction in which the carriers in ISFET die 210 are distorted and the impact this has on resistance.

A feature of an AC generated magnetic field is that the stimulus generated in the output of the ISFET is also AC. High frequency signals will be less impacted by flicker or 1/f noise that occurs in these circuits, thereby giving a higher signal to noise ratio. The frequency approach also lends itself to demodulation techniques that provide good signal to noise vs DC measurements.

The processor unit 230 includes various components, such as signal conditioners, amplifiers, analog to digital (A/D) converters, microprocessor algorithms, and the like, for processing the signals received from ISFET 210 in order to produce a pH measurement.

The sensor apparatus 200 further includes a reference electrode 232 and a counter electrode 234, which are configured to contact the liquid to which ISFET die 210 is exposed. Both of reference electrode 232 and counter electrode 234 are electrically connected to processor unit 230. The counter electrode 234 provides for grounding out parasitic effects and filters out noise that can interfere with sensor measurements.

A sealed magnetic field sensor 236, such as a Hall sensor or other type of magnetometer, can be located adjacent to electromagnet 220 and electrically connected to processor unit 230. The magnetic field sensor 236 provides feedback on the magnitude or state of the electromagnetic field produced by electromagnet 220 to processor unit 230.

A pump can be employed to flow a liquid across ISFET die 210 during operation. The ISFET die 210 can be located within a flow tube that is configured to receive flowing liquid designated by arrows 240.

In one exemplary implementation, ion sensor apparatus 200 is configured to be submersed in sea water, such as for deep sea pH sensing. As such, the various components of ion sensor apparatus 200 can be packaged in a sealed housing structure that is able to withstand deep sea pressure and temperature conditions. Other exemplary implementations for sensor apparatus 200 include ion sensing of ground water, industrial chemicals, refined chemicals, crude oil, and the like.

In a method of compensating for ion sensor measurement errors in sensor apparatus 200, ISFET die 210, while in contact with a liquid such as sea water, is exposed to a magnetic field from electromagnet 220. This produces a corresponding output in resistance of ISFET die 210, which is monitored by processor unit 230 to determine whether there is a difference between this actual output and an expected output based on the magnetic field, and an error compensation value is determined when a difference in the outputs is detected. The error compensation value is then applied to null the difference between the actual output and the expected output.

Figure 3:
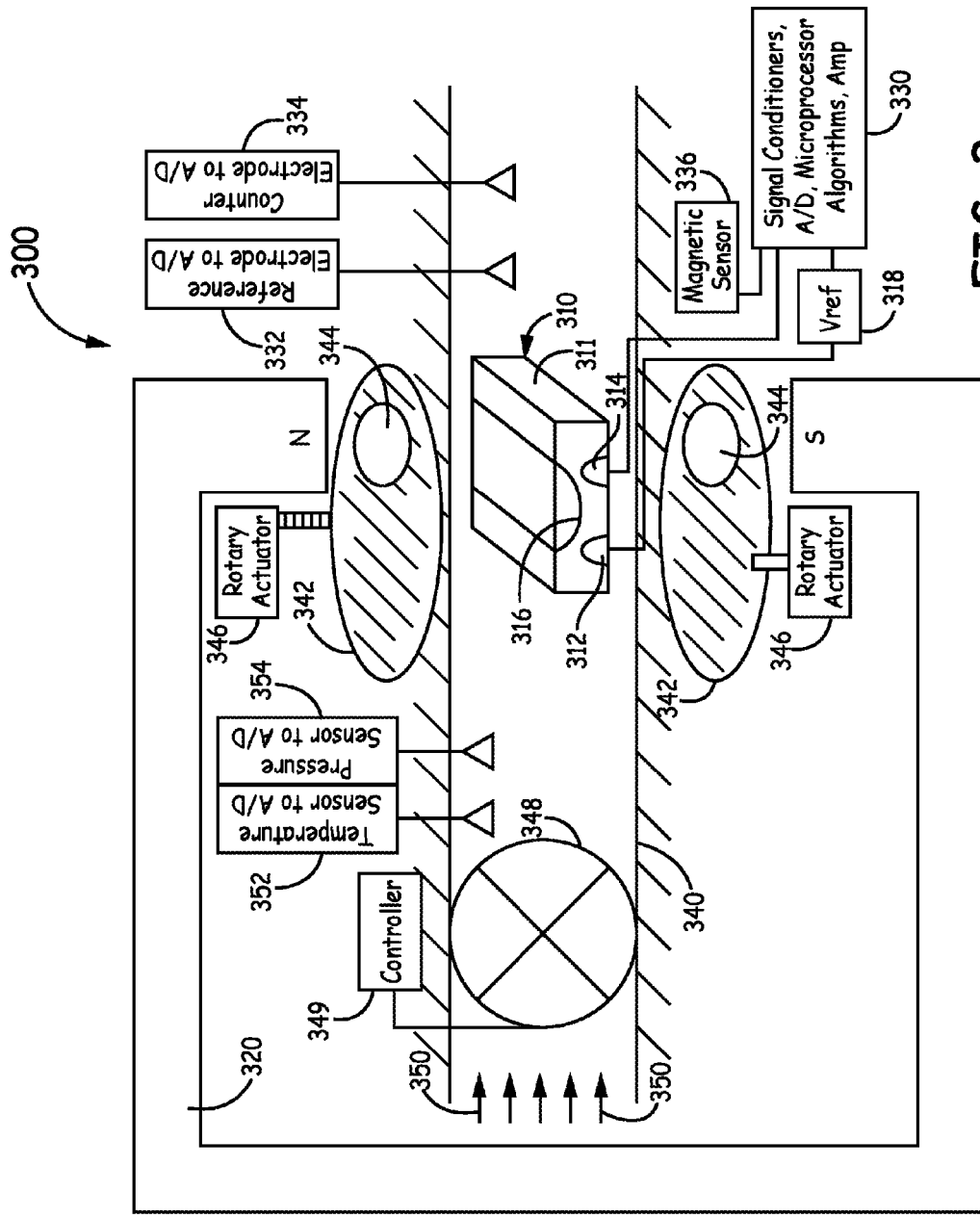
FIG. 3 is a schematic diagram of an ion sensor apparatus according to a further embodiment.

FIG. 3 illustrates an ion sensor apparatus 300 according to another embodiment. The sensor apparatus 300 generally includes an ISFET die 310 configured to be exposed to a liquid, at least one permanent magnet 320 configured to expose ISFET die 310 to a magnetic field, and a processor unit 330 operatively connected to ISFET die 310.

The ISFET die 310 includes a semiconductor substrate 311 such as a silicon substrate. A source 312, a drain 314, and an ion sensitive gate channel 316 are formed in semiconductor substrate 311 with conventional techniques. The source 312 is electrically connected to a voltage reference source 318, which is coupled to processor unit 330. The drain 314 is also electrically connected to processor unit 330. The ISFET die 310 is located within a flow tube 340 that is configured to receive flowing liquid designated by arrows 350.

The permanent magnet 320 is located outside of flow tube 340 but positioned such that ISFET die 310 can be exposed to the magnetic field of permanent magnet 320. A magnetic shield 342 surrounds the outside of flow tube 340 where ISFET die 310 is located. The magnetic shield 342 is configured to intermittently expose ISFET die 310 to the magnetic field of permanent magnet 320.

In one embodiment, the magnetic shield 342 has a disc-shaped structure with holes 344 for exposure of ISFET die 310 to the magnetic field of permanent magnet 320. A rotary actuator 346 can be coupled to magnetic shield 342 to provide rotation of magnetic shield 342, from a closed position that blocks the magnetic field, to an open position that allows ISFET die 310 to be exposed to the magnetic field of permanent magnet 320 when holes 344 are aligned with the north and south magnetic poles (N and S). The operation of rotary actuator 346 can be controlled by processor unit 330 with conventional techniques.

In another embodiment, a pair of permanent magnets can be implemented in sensor apparatus 300, such that ISFET die 310 is exposed to opposite poles of each magnet. For example, ISFET die 310 can be exposed to the magnetic field produced between the N pole of one magnet and the S pole of the other magnet.

The processor unit 330 includes various components, such as signal conditioners, amplifiers, A/D converters, algorithms, and the like, for processing the signals received from ISFET die 310 in order to produce a pH measurement.

The sensor apparatus 300 further includes a reference electrode 332 and a counter electrode 334, which are in communication with the liquid in flow tube 340. Both reference electrode 332 and counter electrode 334 are electrically connected to processor unit 330 through an A/D converter.

A magnetic field sensor 336 is located in line with the magnetic field of permanent magnet 320, and is electrically connected to processor unit 330. The magnetic field sensor 336 provides feedback on the magnitude or state of the magnetic field of permanent magnet 320 to processor unit 330.

In regard to flowing liquid over ISFET die 310, it may be desired that the flow stop during the magnetic stimulus. For example, the combination of flowing electrically conductive water (e.g., sea water) and a magnetic field may generate a current flow or potential on nearby electrodes or ISFET die 310 due to magnetohydrodynamics. Thus, a flow control valve 348 can be positioned near an opening of flow tube 340 to stop the flow of water during the magnetic stimulus of ISFET die 310. The flow control valve 348 can be operated by a controller 349 to open and close to the valve as needed.

The sensor apparatus 300 can also include at least one temperature sensor 352, and a pressure sensor 354, which are in communication with the liquid in flow tube 340. Both of temperature sensor 352 and pressure sensor 354 are electrically connected to processor unit 330 through an A/D converter. In one embodiment, two or more temperature sensors can be arranged spatially around ISFET die 310 to allow for the determination of thermal gradients, which can be used for error compensation.

In one implementation, ion sensor apparatus 300 is configured to be submersed in sea water, such as for deep sea pH sensing. As such, the various components of ion sensor apparatus 300 can be packaged in a sealed housing structure that is able to withstand deep sea pressure and temperature conditions. Other exemplary implementations for sensor apparatus 300 include ion sensing of ground water, industrial chemicals, refined chemicals, crude oil, and the like.

In a method of compensating for ion sensor measurement errors in sensor apparatus 300, ISFET die 310, while in contact with a liquid such as sea water, is exposed to a magnetic field from permanent magnet 320. This produces a corresponding output in resistance of ISFET die 310, which is monitored by processor unit 330 to determine whether there is a difference between this actual output and an expected output based on the magnetic field, and an error compensation value is determined when a difference in the outputs is detected. The error compensation value is then applied to null the difference between the actual output and the expected output.

Figure 4A:
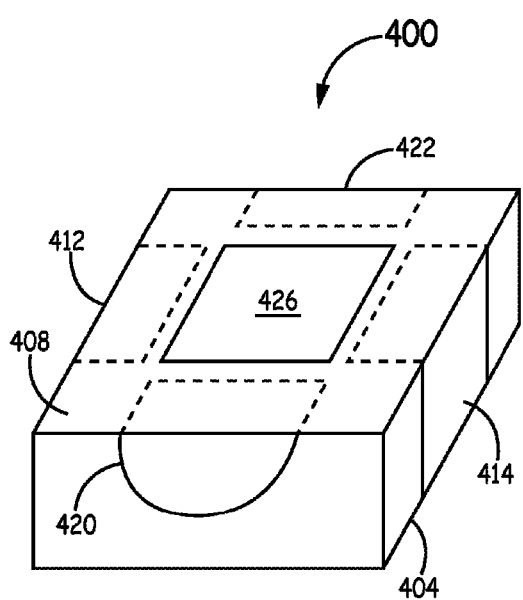
FIG. 4A is a schematic perspective view of a semiconductor device that can be implemented as an Ion Sensitive Field Effect Transistor (ISFET) die according to one embodiment.
Figure 4B:
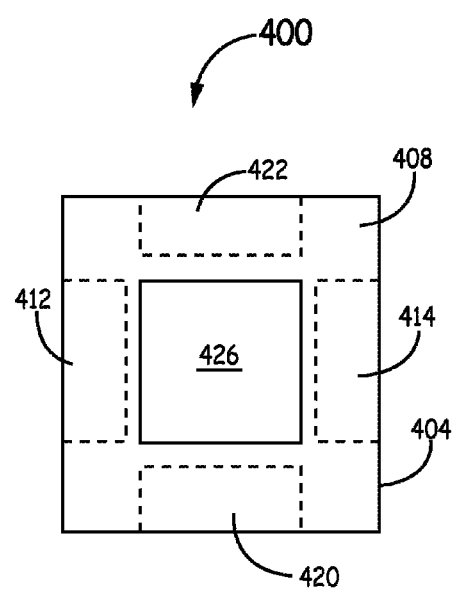
FIG. 4B is a schematic top view of the semiconductor device of FIG. 4A.

FIGS. 4A and 4B illustrate a semiconductor device 400 according to an alternative embodiment, which can be implemented as an ISFET die in the present ion sensor apparatus. The device 400 includes a semiconductor substrate 404 such as a silicon substrate, which has a top surface 408. A source 412 and a drain 414 are located in opposing side portions of substrate 404 below top surface 408. A pair of separate electrical Hall contacts 420 and 422 are located in opposing side portions of substrate 404 below top surface 408 and adjacent to the side portions where source 412 and drain 414 are located. A gate channel 426, which is sensitive to ions in a liquid, is located in a top central portion of substrate 404 between source 412 and drain 414, and between Hall contacts 420, 422. The device 400 can be fabricated using conventional semiconductor processing techniques.

The source 412, drain 414, and Hall contacts 420, 422 are separate from each other, and located below top surface 408 of substrate 411 to avoid contact with a liquid media during operation of device 410 in an ion sensor apparatus. The device 410 allows for measurement of two voltages, with one voltage measurement from Hall contacts 420, 422, and the other voltage measurement from source 412 and drain 414.

Figure 5:
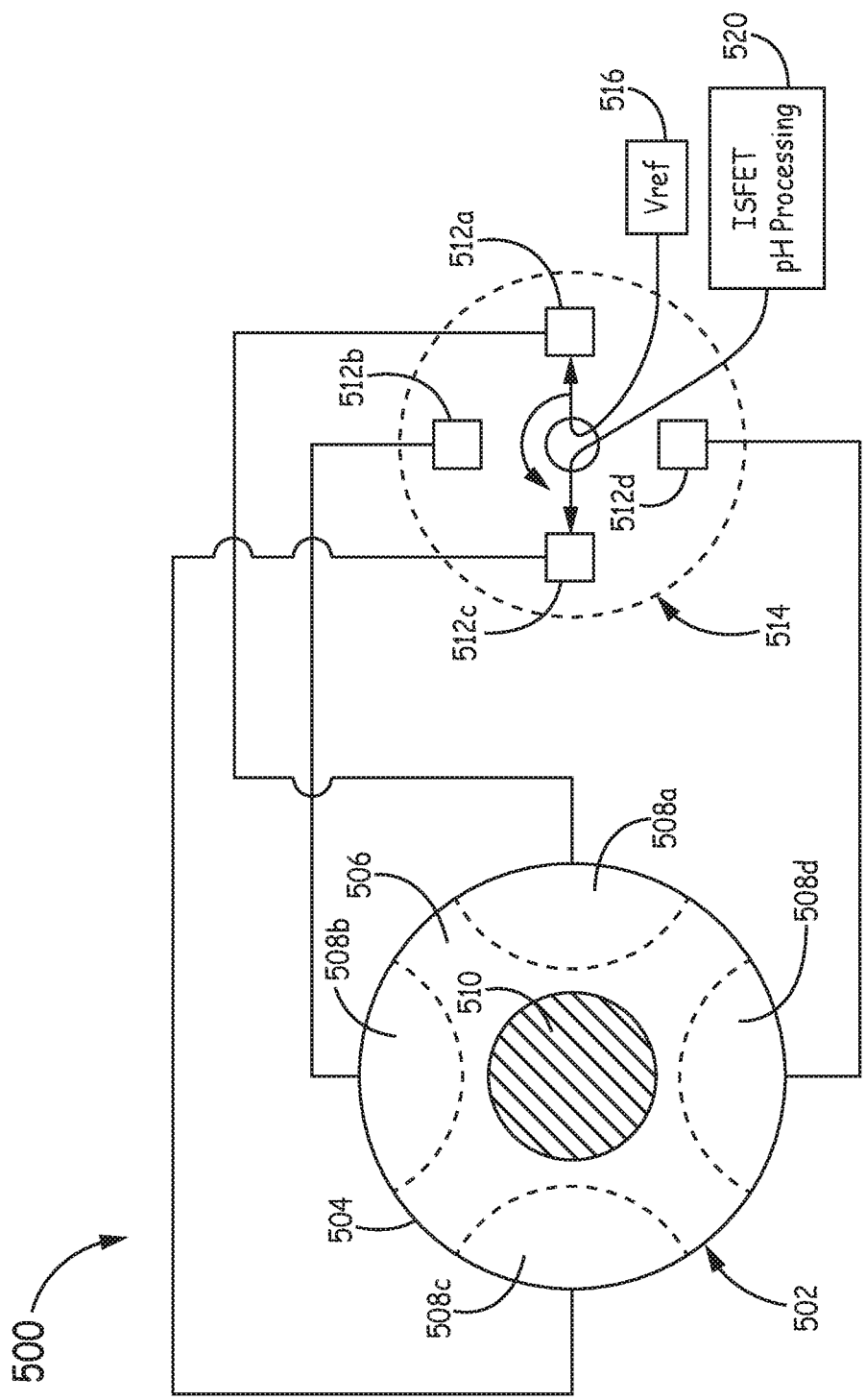
FIG. 5 is a schematic perspective view of a semiconductor device that can be implemented in an ion sensor apparatus according to one embodiment.

FIG. 5 illustrates a semiconductor device 500 according to an alternative embodiment, which can be implemented in the present ion sensor apparatus. The device 500 includes an ion sensitive die 502 comprising a semiconductor substrate 504 such as a silicon substrate, which has a top surface 506. A plurality of contacts, such as contacts 508a-508d, are located in opposing side portions of substrate 504 below top surface 506. An ion sensitive channel 510 is located in a top central portion of substrate 504 between the contacts. The contacts are separate from each other, and located below top surface 506 of substrate 504 to avoid touching a liquid during operation of device 500 in an ion sensor apparatus. Although substrate 504 is depicted as having a circular shape, substrate 504 can be fabricated to have other geometric shapes. The die 502 can be fabricated using conventional semiconductor processing techniques.

Each of contacts 508a-508d is coupled to respective contact pads 512a-512d, which are part of a rotary switch 514. Each of contact pads 512a-512d is switchably connectable to a voltage reference source (Vref) 516 or to a processor unit 520, which can be configured for ISFET pH processing.

During operation, different contacts of ion sensitive die 502 can be selectively connected through rotary switch 514 to act as a source and drain. For example, when Vref 516 is coupled to pad 512a through rotary switch 514, contact 508a is electrically connected to Vref 516 and acts as a source. Also, when processor unit 520 is coupled to pad 512c through rotary switch 514, contact 508c is electrically connected to processor unit 520 and acts as a drain. In another configuration, when Vref 516 is coupled to pad 512b through rotary switch 514, contact 508b is electrically connected to Vref 516 and acts as a source. In this configuration, when processor unit 520 is coupled to pad 512d through rotary switch 514, contact 508d is electrically connected to processor unit 520 and acts as a drain.

Figure 6:
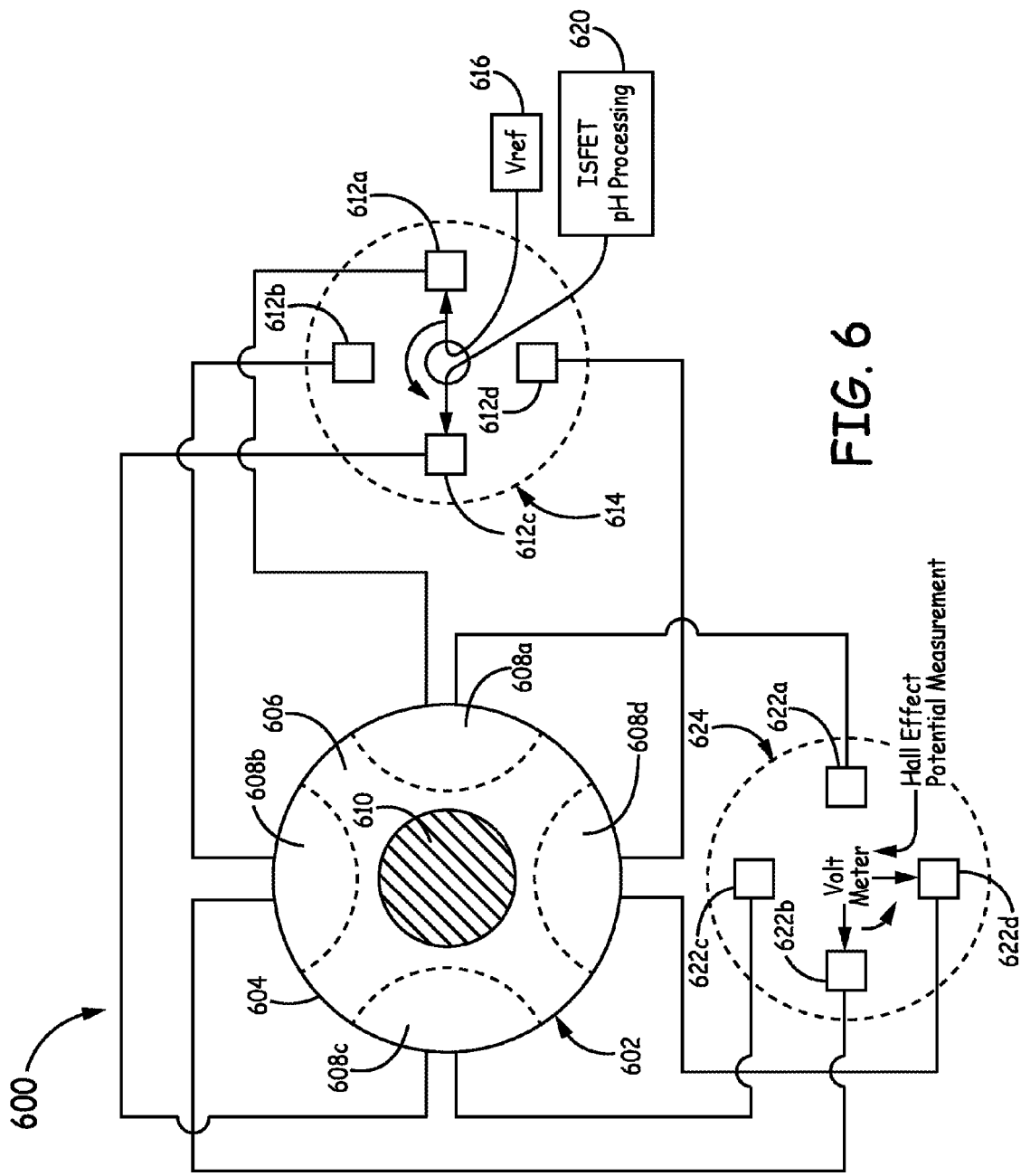
FIG. 6 is a schematic perspective view of a semiconductor device that can be implemented in an ion sensor apparatus according to another embodiment.

FIG. 6 illustrates a semiconductor device 600 according to another alternative embodiment, which can be implemented in the present ion sensor apparatus. The device 600 includes an ion sensitive die 602 that has similar features as die 502 (FIG. 5). Accordingly, die 602 includes a semiconductor substrate 604 that has a top surface 606. A plurality of contacts, such as contacts 608a-608d, are located in opposing side portions of substrate 604 below top surface 606. An ion sensitive channel 610 is located in a top central portion of substrate 604 between the contacts. The contacts are separate from each other, and located below top surface 606 of substrate 604 to avoid touching a liquid being tested.

Each of contacts 608a-608d is coupled to respective contact pads 612a-612d, which are part of a rotary switch 614. Each of contact pads 612a-612d is switchably connectable to a Vref 616 or to a processor unit 620, which can be configured for ISFET pH processing. In addition, each of contacts 608a-608d is coupled to respective contact pads 622a-622d that are part of a rotary switch 624, which is configured for Hall effect potential measurements.

During operation of device 600, opposite orthogonal contacts are connected when making pH measurements and/or Hall potential measurements. Accordingly, different contacts of ion sensitive die 602 can be selectively connected through rotary switch 614 to act as a source and drain. For example, when Vref 616 is coupled to pad 612a through rotary switch 614, contact 608a is electrically connected to Vref 616 and acts as a source. Also, when processor unit 620 is coupled to pad 612c through rotary switch 614, contact 608c is electrically connected to processor unit 620 and acts as a drain.

In addition, those contacts of die 602 not used as the source and drain can be selectively connected to a voltmeter by rotary switch 624 to allow for Hall effect potential measurements. For example, when the voltmeter is coupled to pad 622b through rotary switch 624, contact 608b is electrically connected to the voltmeter and acts as a Hall contact. Likewise, when the voltmeter is coupled to pad 622d through rotary switch 624, contact 608d is electrically connected to the voltmeter and also acts as a Hall contact.

Although the dies in the embodiments of FIGS. 5 and 6 are depicted with four contacts, more contacts can be added to the dies so long as opposite orthogonal contacts are connected when making pH measurements and/or Hall potential measurements.

The dies of FIGS. 5 and 6 can provide various error mitigating benefits when employed. For example, the dies can mitigate errors introduced by a material inhomogeneity in the dies. In addition, the dies can mitigate errors introduced by unintended misalignment between a silicon wafer and semiconductor processing masks, as well as depositions, when patterning the die features during fabrication. Further, the dies can mitigate effects of thermal or mechanical gradients and associated impact on piezoresistance, piezo-Hall, and thermoelectric effects, as well as reduce 1/frequency noise.

A processor used in the present sensor apparatus and method can be implemented using software, firmware, hardware, or any appropriate combination thereof, as known to one of skill in the art. These may be supplemented by, or incorporated in, specially-designed application-specific integrated circuits (ASICs) or field programmable gate arrays (FPGAs). The present method can be implemented by computer executable instructions, such as program modules, which are executed by the processor. Generally, program modules include routines, objects, data components, data structures, algorithms, and the like.

Instructions for carrying out the various process tasks, calculations, and generation of other data used in the operation of the methods described herein can be implemented in software, firmware, or other computer or processor readable instructions. These instructions are typically stored on any appropriate machine readable medium used for storage of computer or processor readable instructions or data structures.

Suitable processor readable media may include storage or memory media such as magnetic or optical media. For example, storage or memory media may include volatile or non-volatile media such as Random Access Memory (RAM); Read Only Memory (ROM), Electrically Erasable Programmable ROM (EEPROM), flash memory, and the like; or any other media that can be used to carry or store desired program code in the form of computer executable instructions or data structures.

EXAMPLE EMBODIMENTS

Example 1 includes an ion sensor apparatus comprising at least one ion sensitive field effect transistor (ISFET) device configured to be exposed to a liquid; a reference electrode configured to contact the liquid to which the ISFET device is exposed; at least one magnet configured to intermittently expose the ISFET device to a magnetic field; and a processor operatively connected to the ISFET device and the reference electrode; wherein the processor modulates the magnetic field to produce a corresponding modulated output in resistance of the ISFET device, and modulation of a reported output value of the ion sensor apparatus.

Example 2 includes the sensor apparatus of Example 1, wherein the at least one magnet comprises an electromagnet.

Example 3 includes the sensor apparatus of Example 2, wherein the electromagnet is selectively activated by the processor to intermittently expose the ISFET device to the magnetic field produced by the electromagnet.

Example 4 includes the sensor apparatus of Example 1, wherein the at least one magnet comprises a permanent magnet.

Example 5 includes the sensor apparatus of Example 4, further comprising a magnetic shield that is configured to intermittently expose the ISFET device to the magnetic field produced by the permanent magnet.

Example 6 includes the sensor apparatus of any of Examples 1-5, further comprising a magnetic field sensor adjacent to the magnet and configured to measure the magnitude or state of the magnetic field.

Example 7 includes the sensor apparatus of any of Examples 1-6, further comprising a counter electrode configured to contact the liquid to which the ISFET device is exposed, wherein the processor is operatively connected to the counter electrode.

Example 8 includes the sensor apparatus of any of Examples 1-7, further comprising at least one temperature sensor and a pressure sensor, wherein the temperature sensor and the pressure sensor are configured to contact the liquid to which the ISFET device is exposed.

Example 9 includes the sensor apparatus of any of Examples 1-8, further comprising a flow tube configured to receive the liquid, wherein the ISFET device is disposed within the flow tube.

Example 10 includes the sensor apparatus of Example 9, further comprising a flow valve that controls the flow of the liquid into the flow tube.

Example 11 includes the sensor apparatus of any of Examples 1-10, wherein the ISFET device comprises a semiconductor substrate having a top surface; a source and a drain located in opposing side portions of the semiconductor substrate; a pair of electrical Hall contacts each located in opposing side portions of the semiconductor substrate that are adjacent to the side portions where the source and drain are located; and a gate channel, which is sensitive to ions in the liquid, located in a top central portion of the semiconductor substrate between the source and the drain, and between the pair of electrical Hall contacts; wherein the source, the drain, and the electrical Hall contacts are separate from each other and located below the top surface of the semiconductor substrate.

Example 12 includes the sensor apparatus of any of Examples 1-11, wherein the reported output value is a pH measurement of the liquid.

Example 13 includes a method of compensating for ion sensor measurement errors, the method comprising contacting a liquid with a portion of an ISFET device; exposing the ISFET device to a modulated magnetic field to produce a corresponding modulated output in resistance of the ISFET device; monitoring the modulated output to determine whether there is a difference between the modulated output and an expected output based on the modulated magnetic field; determining an error compensation value when there is a difference between the modulated output and the expected output; and applying the error compensation value to null the difference between the modulated output and the expected output over a period of time to maintain stability of ion sensor measurements.

Example 14 includes the method of Example 13, wherein the modulated magnetic field is from an electromagnet.

Example 15 includes the method of Example 14, wherein the electromagnet is selectively activated by a processor to expose the ISFET device to the modulated magnetic field.

Example 16 includes the method of Example 13, wherein the modulated magnetic field is from at least one permanent magnet.

Example 17 includes the method of any of Examples 13-16, wherein the liquid comprises sea water, ground water, industrial chemicals, refined chemicals, or crude oil.

Example 18 includes the method of any of Examples 13-17, wherein the ISFET device is configured to measure a pH of the liquid.

Example 19 includes a semiconductor device comprising a semiconductor substrate having a top surface; a plurality of contacts located in opposing side portions of the semiconductor substrate; and an ion sensitive channel located in a top central portion of the semiconductor substrate between the contacts; wherein the contacts are separate from each other and located below the top surface of the semiconductor substrate.

Example 20 includes the device of Example 19, and further comprising one or more rotary switches that selectively couple the contacts to one or more voltage sources, such that the contacts are electrically configured for taking a pH measurement or a Hall effect potential measurement when the semiconductor device is employed in an ion sensor apparatus.

The present invention may be embodied in other specific forms without departing from its essential characteristics. The described embodiments are to be considered in all respects only as illustrative and not restrictive. The scope of the invention is therefore indicated by the appended claims rather than by the foregoing description. All changes that come within the meaning and range of equivalency of the claims are to be embraced within their scope.

What is claimed is:

1. An ion sensor apparatus, comprising:
   at least one ion sensitive field effect transistor (ISFET) device configured to be exposed to a liquid;
   a reference electrode configured to contact the liquid to which the ISFET device is exposed;
   at least one magnet configured to intermittently expose the ISFET device to a magnetic field;
   a processor operatively connected to the ISFET device and the reference electrode; and
   a non-transitory processor readable medium including instructions, executable by the processor, to perform a method of compensating for ion sensor measurement errors, the method comprising:
     modulating the magnetic field to produce a corresponding modulated output in resistance of the ISFET device;
     monitoring the modulated output to determine whether there is a difference between the modulated output and an expected output based on the modulated magnetic field;
     determining an error compensation value when there is a difference between the modulated output and the expected output; and
     applying the error compensation value to null the difference between the modulated output and the expected output over a period of time to maintain stability of ion sensor measurements.

2. The sensor apparatus of claim 1, wherein the at least one magnet comprises an electromagnet.

3. The sensor apparatus of claim 2, wherein the electromagnet is selectively activated by the processor to intermittently expose the ISFET device to the magnetic field produced by the electromagnet.

4. The sensor apparatus of claim 1, wherein the at least one magnet comprises a permanent magnet.

5. The sensor apparatus of claim 4, further comprising a magnetic shield that is configured to intermittently expose the ISFET device to the magnetic field produced by the permanent magnet.

6. The sensor apparatus of claim 1, further comprising a magnetic field sensor adjacent to the magnet and configured to measure the magnitude or state of the magnetic field.

7. The sensor apparatus of claim 1, further comprising a counter electrode configured to contact the liquid to which the ISFET device is exposed, wherein the processor is operatively connected to the counter electrode.

8. The sensor apparatus of claim 1, further comprising at least one temperature sensor and a pressure sensor, wherein the temperature sensor and the pressure sensor are configured to contact the liquid to which the ISFET device is exposed.

9. The sensor apparatus of claim 1, further comprising a flow tube configured to receive the liquid, wherein the ISFET device is disposed within the flow tube.

10. The sensor apparatus of claim 9, further comprising a flow valve that controls the flow of the liquid into the flow tube.

11. The sensor apparatus of claim 1, wherein the ISFET device comprises:
   a semiconductor substrate having a top surface;
   a source and a drain located in opposing side portions of the semiconductor substrate;
   a pair of electrical Hall contacts each located in opposing side portions of the semiconductor substrate that are adjacent to the side portions where the source and drain are located; and
   a gate channel, which is sensitive to ions in the liquid, located in a top central portion of the semiconductor substrate between the source and the drain, and between the pair of electrical Hall contacts;
   wherein the source, the drain, and the electrical Hall contacts are separate from each other and located below the top surface of the semiconductor substrate.

12. The sensor apparatus of claim 1, wherein a reported output value is a pH measurement of the liquid.

* * * * *